(12) United States Patent
Saito et al.

(10) Patent No.: US 7,740,908 B2
(45) Date of Patent: Jun. 22, 2010

(54) METHOD FOR FORMING A FILM BY SPIN COATING

(75) Inventors: Yukou Saito, Kanagawa (JP); Masashi Hakamata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1120 days.

(21) Appl. No.: 11/362,741

(22) Filed: Feb. 28, 2006

(65) Prior Publication Data

US 2007/0259193 A1    Nov. 8, 2007

(30) Foreign Application Priority Data

Feb. 28, 2005  (JP)  .............................. 2005-052417
Feb. 28, 2005  (JP)  .............................. 2005-052419

(51) Int. Cl.
*B05D 3/12* (2006.01)
*B05D 3/04* (2006.01)

(52) U.S. Cl. ....................... 427/240; 427/335; 427/425; 118/52; 118/320

(58) Field of Classification Search ................. 427/240, 427/425, 335; 118/52, 320
See application file for complete search history.

(56) References Cited

U.S. PATENT DOCUMENTS

| | | | | |
|---|---|---|---|---|
| 4,347,302 A | * | 8/1982 | Gotman | 430/270.1 |
| 5,472,502 A | * | 12/1995 | Batchelder | 118/52 |
| 6,027,760 A | * | 2/2000 | Gurer et al. | 427/8 |
| 7,030,039 B2 | * | 4/2006 | Gurer et al. | 438/780 |
| 2005/0147748 A1 | * | 7/2005 | Nguyen | 427/230 |
| 2005/0170354 A1 | * | 8/2005 | Munch-Fals | 435/6 |

FOREIGN PATENT DOCUMENTS

| | | |
|---|---|---|
| JP | 3231970 B2 | 8/1996 |
| JP | 2942213 B2 | 3/1998 |
| JP | 3352371 B2 | 5/1999 |
| JP | 3273754 B2 | 7/1999 |

* cited by examiner

*Primary Examiner*—Kirsten C Jolley
(74) *Attorney, Agent, or Firm*—Sughrue Mion, PLLC

(57) ABSTRACT

It is an object of the present invention to provide a method for producing a solid substrate used for sensors having a film with a small film thickness distribution, and a solid surface used for sensors having a film with a small film thickness distribution. The present invention provides a method for producing a solid substrate for sensors that has a coating on the surface using spin coating, wherein a substrate to be coated is rotated in an atmosphere in which the vapor pressure of coating solvent is 50% to 100% with respect to the saturation vapor pressure so as to form a thin film of a coating solution on said substrate to be coated.

5 Claims, No Drawings

METHOD FOR FORMING A FILM BY SPIN COATING

TECHNICAL FIELD

The present invention relates to a method for forming a thin film with a small film thickness distribution, and a solid substrate for sensors having a film with a small film thickness distribution. More specifically, the present invention relates to a solid substrate for sensors, the surface of which is coated with a thin polymer film, and a production method thereof.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

As a thin film having a functional group capable of immobilizing a physiologically active substance, there has been reported a measurement chip where a physiologically active substance is immobilized by using a functional group binding to metal, a linker with a chain length of 10 or more atoms, and a compound having a functional group capable of binding to the physiologically active substance (Japanese Patent No. 2815120). Moreover, a measurement chip comprising a metal film and a plasma-polymerized film formed on the metal film has been reported (Japanese Patent Laid-Open No. 9-264843).

On the other hand, when a specific binding reaction is measured between a physiologically active substance and a test substance, the test substance does not necessarily consist of a single component, but it is sometimes required to measure the test substance existing in a heterogeneous system, such as in a cell extract. In such a case, if various contaminants such as proteins or lipids were non-specifically adsorbed on the detection surface, detection sensitivity in measurement would significantly be decreased. The aforementioned detection surface has been problematic in that such non-specific adsorption often takes place thereon.

A thin film formation method involving spin coating comprises adding a coating solution dropwise to a substrate to be coated and drawing the coating solution thereon by centrifugal force, so as to form a thin film. However, this method is problematic in that film thickness distribution is likely to occur. In order to solve such a problem, several methods have been studied. For example, a method comprising adding a coating solution dropwise to a substrate to be coated and then rotating the substrate in a hermetically sealed inner cup has been reported (Japanese Patent No. 2942213). As a modified method thereof, a method comprising spin coating while injecting thin gas into the inner cup has also been reported (Japanese Patent No. 3231970). However, these methods could not sufficiently prevent unevenness in the film thickness generated in the marginal part of the substrate.

DISCLOSURE OF INVENTION

It is an object of the present invention to solve the aforementioned problems of the prior art techniques. In other words, it is an object of the present invention to provide a method for producing a solid substrate used for sensors having a film with a small film thickness distribution, and a solid surface used for sensors having a film with a small film thickness distribution. In particular, it is an object of the present invention to provide a method for producing a solid substrate used for sensors, the surface of which is coated with a thin polymer film with a small film thickness distribution, and a solid substrate used for sensors, the surface of which is coated with a thin polymer film with a small film thickness distribution.

As a result of intensive studies directed towards achieving the aforementioned objects, the present inventors have found that a solid substrate used for sensors having a thin film with a small film thickness distribution can be formed by rotating a substrate to be coated in an atmosphere where the vapor pressure of the coating solution is 50% to 100% with respect to the saturation vapor pressure in spin coating, whereby the coating solution on the substrate to be coated is made into a thin film. In addition, the present inventors could form a solid substrate used for sensors having a thin film with a small film thickness distribution by the following spin coating process: the surface of a substrate to be coated is coated with a coating solution; the substrate is introduced into a container with a sealed structure where the substrate is kept in a substantially non-rotating state for 10 to 4000 seconds; and then the substrate is rotated for spin coating. In addition, the present inventors have demonstrated that when a solid substrate used for sensors that is coated with a thin film formed by the above method is used, deviation in sensitivity due to unevenness in the film thickness can be suppressed. The present invention has been completed based on these findings.

Thus, the present invention a method for producing a solid substrate for sensors that has a coating on the surface using spin coating, wherein a substrate to be coated is rotated in an atmosphere in which the vapor pressure of coating solvent is 50% to 100% with respect to the saturation vapor pressure so as to form a thin film of a coating solution on said substrate to be coated.

Preferably, said substrate to be coated is introduced into a sealed container, and said substrate to be coated is rotated in an atmosphere in which the vapor pressure of coating solvent is 50% to 100% with respect to the saturation vapor pressure.

Preferably, the volume of said sealed container into which said substrate to be coated is introduced is 3 to 1000 times the volume of the coating solution with which the surface of said substrate to be coated is coated.

Preferably, said substrate to be coated is set on an inner cup at a position such that the distribution of the centrifugal force on said substrate to be coated, which is produced by the rotation of an inner cup, is such that the centrifugal force at its maximum point is 100 times or less the centrifugal force at its minimum point, the coating solution is added dropwise onto the surface of said substrate to be coated, and then said substrate to be coated is rotated.

Preferably, the surface of said substrate to be coated is coated with the coating solution, said substrate to be coated is introduced into a container having a sealed structure, said substrate to be coated is kept in a substantially non-rotating state for 10 to 4000 seconds, and said substrate to be coated is rotated so as to form a thin film on the substrate.

In another aspect, the present invention provides a solid substrate for sensors that has a coating on the surface, which is produced by the method of the present invention.

Preferably, the coating is a hydrophobic polymer layer, and the solid substrate has a surface modification layer as the outermost layer from the substrate.

Preferably, the surface modification layer has a functional group capable of generating a covalent bond.

Preferably, the solid substrate for sensors according to the present invention has a metal layer between the solid substrate and the hydrophobic polymer layer.

Preferably, the metal layer consists of a free-electron metal selected from the group consisting of gold, silver, copper, platinum, and aluminum.

Preferably, the solid substrate for sensors according to the present invention has a functional group capable of immobilizing a physiologically active substance on the outermost surface of the substrate.

Preferably, the functional group capable of immobilizing a physiologically active substance is —OH, —SH, —COOH, —NR$^1$R$^2$ (wherein each of R$^1$ and R$^2$ independently represents a hydrogen atom or a lower alkyl group), —CHO, —NR$^3$NR$^1$R$^2$ (wherein each of R$^1$, R$^1$, and R$^3$ independently represents a hydrogen atom or a lower alkyl group), —NCO, —NCS, an epoxy group, or a vinyl group.

Preferably, the solid substrate for sensors according to the present invention is used for non-electrochemical detection. More preferably, it is used for surface plasmon resonance analysis.

Preferably, a physiologically active substance is bound to the surface of the solid substrate for sensors according to the present invention.

In another aspect, the present invention provides a method for detecting or measuring a substance interacting with a physiologically active substance, which comprises: a step of allowing a physiologically active substance to come into contact with the surface of the solid substrate for sensors according to the present invention, so as to immobilize it thereon; and a step of allowing the obtained solid substrate for sensors, to the surface of which the physiologically active substance is bound, to come into contact with a test substance.

BEST MODE FOR CARRYING OUT THE INVENTION

The embodiments of the present invention will be described below.

The method for producing a solid substrate for sensors according to the present invention is characterized in that, in the spin coating, a substrate to be coated is rotated in an atmosphere in which the vapor pressure of coating solvent is 50% to 100% with respect to the saturation vapor pressure so as to form a thin film of a coating solution on said substrate to be coated.

The vapor pressure of the coating solution can be made 50% or more and 100% or less with respect to the saturation vapor pressure by introducing the solvent vapor into the sealed container from the outside, or by separately introducing the coating solution into the sealed container, for example. In accordance with the invention, the vapor pressure of the coating solution may be 50% to 100% (namely, 50% or more and 100% or less), and preferably 60% to 100%, and more preferably 70% to 100% with respect to the saturation vapor pressure.

A solid substrate for sensors having a coating on the surface thereof manufactured according to the method of the invention is characterized in that it has a small distribution of film thickness. The film thickness distribution of the coating on the surface can be evaluated by the ellipsometry method using equipment such as the In-Situ Ellipsometer MAUS-101 manufactured by Five Lab Co., Ltd., for example. Preferably, the variation coefficient of the film thickness of the solid substrate for sensors according to the invention is 10% or less and more preferably 8% or less. The film thickness distribution can also be evaluated by observing the distribution of fluorescent intensity on the spin-coated substrate using a black light or the like, for example. When the distribution of fluorescent intensity on the substrate having a coating on the surface thereof manufactured by the method of the invention is observed using a black light or the like, the fluorescent intensity is preferably observed substantially uniformly. Alternatively, the film thickness distribution can be evaluated by measuring changes in the SPR signal as an analyte is caused to interact with ligands immobilized on the spin-coated substrate, and then measuring the variation coefficient (percentage value of the standard deviation divided by an average value) of the change in the signal depending on the location in the chip. In the case of the solid substrate for sensors manufactured by the method of the invention, the variation coefficient of the signal change is preferably 10% or less, and more preferably 8% or less, and most preferably 5% or less.

In the method for manufacturing a solid substrate for sensors according to the present invention, the surface of a substrate to be coated is preferably coated with a coating solution, the coated substrate is introduced into a container having a sealed structure, the substrate is kept in a substantially non-rotating state for 10 to 4000 seconds, and then the coated substrate is rotated, whereby a thin film is formed on the substrate. By the term "substantially non-rotating state", it is herein meant that the coating solution on the substrate does not become scattered outside the substrate to be coated due to movement. Within such a range, the substrate may be concentrically moved at a low rpm. Transferring the substrate or moving it in a concentric motion for operation verification purposes are included in the term "substantially non-rotating state." The time in which the substantially non-rotating state is kept is preferably 15 to 180 seconds.

The volume of the sealed container into which the substrate to be coated is introduced is preferably 3 to 1000 times the volume of the coating solution with which the substrate to be coated is coated. More preferably, the volume is 10 to 500 times. If the volume of the sealed container is small, the coating solution that has been scattered from the substrate during spin coating could potentially contaminate the substrate. If the volume is large, it takes more time for the sealed container to be filled with the solvent vapor prior to the rotation of the substrate, potentially affecting the concentration of the coating solution.

The position in which the substrate to be coated is set on the inner cup of the spin coater is preferably such that the distribution of the centrifugal force produced on the substrate to be coated by the rotation thereof is such that the centrifugal force at its maximum point is 100 times or less than the centrifugal force at its minimum point. More preferably, the position in which the substrate to be coated is set is such that the centrifugal force produced on the substrate to be coated by the rotation thereof is such that the centrifugal force at its maximum point is 10 times or less the centrifugal force at its minimum point. Therefore, the size of the substrate is preferably smaller, and the position in which the substrate is set is preferably not over the center of rotation but spaced apart therefrom.

In the present invention, the substrate to be coated can preferably be rotated while the development of the flow of gas toward the substrate is suppressed. Preferably, all or part of the substrate to be coated is enclosed by a container or a wall having sides other than the concentric circle of rotation of the inner cup, whereby the flow of gas toward the substrate can be suppressed.

In the present invention, the surface of the substrate to be coated to which the coating solution is added dropwise is not particularly limited and may therefore be a top surface, a lateral surface, or a bottom surface.

Preferably, the percentage of the surface of the substrate to be coated that is covered with the dropwise-added coating solution is 80% or more and 100% or less and more preferably 90% or more and 100% or less.

A coating solution used in the present invention is preferably a hydrophobic polymer solution. A hydrophobic polymer that can be used in the present invention is substantially insoluble in water. Specifically, such a hydrophobic polymer has solubility in water of less than 0.1%. A hydrophobic polymer preferably contains 30% to 100% by weight of monomer having solubility in water at 25° C. of 0% to 20% by weight.

A hydrophobic monomer which forms a hydrophobic polymer can be selected from vinyl esters, acrylic esters, methacrylic esters, olefins, styrenes, crotonic esters, itaconic diesters, maleic diesters, fumaric diesters, allyl compounds, vinyl ethers, vinyl ketones, or the like. The hydrophobic polymer may be either a homopolymer consisting of one type of monomer, or copolymer consisting of two or more types of monomers.

Examples of a hydrophobic polymer that is preferably used in the present invention may include polystyrene, polyethylene, polypropylene, polyethylene terephthalate, polyvinyl chloride, polymethyl methacrylate, polyester, and nylon.

A hydrophobic polymer used in the present invention preferably has low water content. A preferred range of such water content is between 0.0001% and 0.1%. Specifically, water content is measured in accordance with the method described in ISO62. A hydrophobic polymer sheet with a square of 60 mm and a thickness of 1 mm is produced by the cast method, and the weight (W1) is then measured. Thereafter, this sheet is immersed in distilled water at 23° C. for 24 hours. After completion of the immersion, water on the surface of the sheet is wiped off, and the weight (W2) is then measured. Water content (%) is defined as (W2-W1)/W1×100.

The solvent in the coating solution, such as a hydrophobic polymer solution, is not particularly limited and may be any solvent as long as it dissolves part of the hydrophobic polymer. Examples include but are not limited to formaldehyde solvents such as N,N-dimethylformaldehyde, nitrile solvents such as acetonitrile, alcohol solvents such as phenoxyethanol, ketone solvents such as methyl isobutyl ketone or 2-butanone, and benzene solvents such as toluene.

The thickness of the hydrophobic polymer layer is not particularly limited. The total thickness of all the laminated polymer layers is preferably between 0.1 nm and 500 nm, and particularly preferably between 1 nm and 300 nm.

The substrate of the present invention preferably has a functional group capable of immobilizing a physiologically active substance on the outermost surface of the substrate. The term "the outermost surface of the substrate" is used to mean "the surface, which is farthest from the substrate," and more specifically, it means "the surface of a hydrophobic polymer applied on a substrate, which is farthest from the substrate."

In the present invention, preferably, after the hydrophobic polymer solution such as that mentioned above is brought into contact with the solid substrate, the resultant solid substrate can be subjected to surface modification. An appropriate method for surface modification can be selected from chemical treatments using chemical agents, coupling agents, surfactants or surface evaporation, and physical treatments using heating, ultraviolet rays, radioactive rays, plasma, or ions.

It is preferable that a functional group capable of generating a covalent bond as a result of surface modification be introduced. Preferred functional group includes —OH, —SH, —COOH, —NR$^1$R$^2$ (wherein each of R$^1$ and R$^2$ independently represents a hydrogen atom or lower alkyl group), —CHO, —NR$^3$NR$^1$R$^2$ (wherein each of R$^1$, R$^2$ and R$^3$ independently represents a hydrogen atom or lower alkyl group), —NCO, —NCS, an epoxy group, or a vinyl group. The number of carbon atoms contained in the lower alkyl group is not particularly limited herein. However, it is generally about C1 to C10, and preferably C1 to C6.

In order to introduce these functional groups into the surface, a method is applied that involves applying a hydrophobic polymer containing a precursor of such a functional group on a metal surface or metal film, and then generating the functional group from the precursor located on the outermost surface by chemical treatment. For example, polymethyl methacrylate, a hydrophobic polymer containing —COOCH$_3$ group, is applied on a metal film, and then the surface comes into contact with an NaOH aqueous solution (1N) at 40° C. for 16 hours, so that a —COOH group is generated on the outermost surface. In addition, when a polystyrene coating layer is subjected to a UV/ozone treatment for example, a —COOH group and a —OH group are generated on the outermost surface thereof.

A solid substrate used in the present invention is interpreted in the broadest sense. It indicates a base for supporting materials having functions. It includes not only hard materials, but also flexible materials such as a film or a sheet.

The solid substrate used in the present invention is preferably a metal surface or metal film, which is coated with a hydrophobic polymer. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

The solid substrate of the present invention has as broad a meaning as possible, and means a sensor which converts an interaction between biomolecules into a signal such as an electric signal, so as to measure or detect a target substance. The solid substrate used for sensor according to the present invention can be used as a biosensor. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

A physiologically active substance is covalently bound to the above-obtained solid substrate for sensor via the above functional group, so that the physiologically active substance can be immobilized on the metal surface or metal film.

A physiologically active substance immobilized on the substrate for sensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

A biosensor to which a physiologically active substance is immobilized as described above can be used to detect and/or measure a substance which interacts with the physiologically active substance.

In the present invention, it is preferable to detect and/or measure an interaction between a physiologically active substance immobilized on the solid substrate for sensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta SP$), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta SP$) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta SP$) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta$SP) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta$SP) is measured periodically after the elapse of a certain time, and it is determined whether or not a change has occurred in the above attenuated total reflection angle ($\theta$SP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle ($\theta$SP). For example, a sample solution may be added to a sensing substance, and the amount of an attenuated total reflection angle ($\theta$SP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle ($\theta$SP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle ($\theta$SP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example 1

Preparation of a Sensor Chip 1 According to the Present Invention and Evaluation of Performance thereof (1) Preparation of a Gold-surface Substrate A glass substrate measuring 8 mm in length×120 mm in width×0.5 mm in depth was coated with chromium to a thickness of 2 nm by sputtering using a parallel-beam 6-inch sputtering apparatus (SH-550 from ULVAC Inc.). On the chromium, a gold film was further formed by sputtering to a thickness of 50 nm. The substrate was then treated for 30 minutes with a Model-208 UV-Ozone Cleaning System (TECHNOVISION INC.), thereby preparing a gold-surface substrate.

(2) Preparation of a Coating Solution 1.9 g of poly(3,3,4,4,5,5,6,6,7,7,8,8,8-tridecafluoro octylacrylate)-poly(benzyl methacrylate) copolymer (monomer weight ratio 4/6, weight-average molecular weight 30,000; to be hereafter referred to as "polymer A") was dissolved in methylisobutylketone, and methylisobutylketone was added thereto such that the amount of the solution reached 100 mL. This polymer A solution was then filtered with a 0.45-µm filter, thereby preparing coating solution A. The methylisobutylketone used had been dehydrated beforehand with a molecular sieves 4A 1/16 for 16 hours.

(3) Preparation of a Polymer-A-coated Chip

The gold-surface substrate produced in the above was set within an aluminum container having a sealed structure and measuring 30 mm in length×130 mm in width and 10 mm in depth. The aluminum container had an openable air hole structure having a diameter of 10 mm in the top plate portion, allowing the solvent vapor inside to be diluted as necessary. The aluminum container was fixed on the inner cup of a spin coater (MODEL SC408 (Special) from Nanometric Technology Inc.) having sealed type inner cup such that the gold-surface substrate had its long axis disposed in a tangential manner with respect to a circular arc at a position 135 mm from the center thereof. 100 µL of coating solution A was added dropwise onto the gold-surface substrate using a micropipette, and the entire surface of the gold-surface substrate was coated with coating solution A. The aluminum container was then sealed, allowed to stand for 30 seconds, and rotated at 200 rpm for 60 seconds. The saturation vapor pressure inside the aluminum container immediately before the start of rotation was 90% with respect to the solvent vapor pressure. The volume within the container was 390 times the volume of the coating solution used. After allowing the substrate to stand for 5 minutes in the sealed container, the substrate was removed from the sealed container and allowed to dry overnight at room temperature and atmospheric pressure, thereby obtaining a polymer-A-coated chip.

When the distribution of film thickness was measured in an area across the center of the substrate with a width of 120 mm and at intervals of 0.1 mm by the ellipsometry method (using In-Situ Ellipsometer MAUS-101 from Five Lab Co., Ltd.), the average film thickness was found to be 20 nm and the variation coefficient of the film thickness (percentage value of the standard deviation divided by the average value) was found to be 4%.

(4) Preparation of a Biosensor Chip

The polymer-A-coated chip produced above was immersed in a 1N NaOH aqueous solution, the temperature of which was maintained at 60° C., for 16 hours, and then washed within a jet of pure water, thereby producing a biosensor chip in which a COOH group had been introduced onto the surface of the polymer-A coated layer.

(5) Immobilization of Protein A

The spin-coated chip produced by the above method was brought into contact with a mixture of 1-ethyl-2,3-dimethylaminopropylcarbodiimide (200 mM) and N-hydroxysuccinimide (50 mM) for 30 minutes and was then washed with pure water. The chip was then brought into contact with Protein A (from Nacalai Tesque Inc.) solution (100 μg/mL, 50 mM acetic acid buffer, pH 4.5) for 30 minutes, followed by washing with a 50 mM acetic acid buffer (pH 4.5).

Further, after being brought into contact with an ethanolamine-HCl solution (1M, pH 8.5) for 30 minutes, the spin-coated chip was washed with a 50 mM acetic acid buffer (pH 4.5) so as to block the activated COOH group that had remained without reacting with Protein A.

After being brought into contact with a NaOH aqueous solution (10 mM) for 1 minute, the spin-coated chip was washed with HBS-EP buffer (0.01 mol/L of HEPES (N-2-Hydroxyethylpiperazine-N'-2-ethanesulfonic Acid)(pH7.4), 0.15 mol/L of NaCl, 0.003 mol/L of EDTA, and 0.005% by weight of Surfactant P20, from Biacore), thereby removing Protein A that had been non-specifically adsorbed on the surface of the spin-coated chip. The resultant sample is referred to as Protein-A-immobilized chip.

(6) Detection of a Mouse IgG Binding Signal

Regardless of the detection position of the Protein-A-immobilized chip, the more stable the binding signal, the higher the reliability of the experiment. The dependency of the amount of binding of mouse IgG on the position of the Protein-A-immobilized chip was evaluated by the following method.

Each of Protein-A-immobilized chips produced by the above procedure (1) was set on a surface plasmon resonance measuring apparatus (SPR resonance apparatus shown in FIG. 5 of Applied Spectroscopy, 42(8), 1375-1379 (1988)). Each chip was set at a position such that the central position thereof, at which the laser light was impinged, was at the center in the lengthwise direction and the side thereof was set 10 mm from the edge. Each chip was covered with a polypropylene member, thereby producing a cell measuring 1 mm in width (in the longitudinal direction)×7.5 mm in length (in the lateral direction)×1 mm in depth.

After filling the measurement cells with an HBS-EP buffer, measurement was started. The inside of the cell was replaced with a mouse IgG (from COSMO BIO CO., LTD.) solution (10 μg/mL, HBS-EP buffer), and then the cell was allowed to stand for 5 minutes. Signal change after the 5 minutes was calculated.

The inside of the cell was further brought into contact with an NaOH aqueous solution (10 mM) for one minute and then washed with a HBS-EP buffer whereby, it was confirmed, the binding of the mouse IgG was eliminated and the signal returned to the baseline.

The chip was further immobilized at a position 10 mm away from the edge in the lateral direction, and the measurement of binding of the mouse IgG was similarly conducted.

The chips were further set at 10 mm intervals from the edge in the lateral direction, and a 7-point measurement was conducted on each Protein-A-immobilized chip. The measurement results are shown in Table 1.

Example 2

Preparation of a Sensor Chip 2 of the Present Invention and Evaluation of Performance thereof Spin coating was conducted in the same method as in Example 1 except that, in the production of the polymer-A-coated chip in Example 1(3), the internal measurements of the aluminum container were 30 mm in length×130 mm in width×30 mm in depth. The solvent vapor pressure inside the aluminum container immediately before the start of rotation was 80% with respect to the saturation vapor pressure. The volume inside the container was 1200 times the volume of the coating solution. The average film thickness was found to be 20 nm based on ellipsometric measurement, and the variation coefficient of the film thickness (percentage value of the standard deviation divided by the average value) was found to be 6%. Further, the operations (4) to (6) of Example 1 were carried out.

Comparative Example 1

Preparation of a Sensor Chip 1 According to a Comparative Example and Evaluation of Performance thereof Spin coating was conducted by the same method as in Example 1 except that, in the production of the polymer-A-coated chip in Example 1(3), the opening and closing of the air opening in the aluminum container were adjusted and the solvent vapor pressure inside the aluminum container immediately before the start of rotation following the 30-second rest period was adjusted to be 40% with respect to the saturation vapor pressure. Based on ellipsometric measurement, the average film thickness was found to be 20 nm and the variation coefficient of the film thickness (a percentage value of the standard deviation divided by the average value) was found to be 12%. Further, the operations (4) to (6) of Example 1 were carried out.

Comparative Example 2

Preparation of a Sensor Chip 2 According to a Comparative Example and Evaluation of Performance thereof Spin coating was conducted by the same method as in Example 2 except that, in the production of the polymer-A-coated chip in Example 2, the opening and closing of the air opening in the aluminum container were adjusted and the solvent vapor pressure inside the aluminum container immediately before the start of rotation following the 30-second rest period was adjusted to be 30% with respect to the saturation vapor pressure. Based on ellipsometric measurement, the average film thickness was found to be 20 nm and the variation coefficient of the film thickness (a percentage value of the standard deviation divided by the average value) was found to be 14%. Further, the operations (4) to (6) of Example 1 were carried out.

Comparative Example 3

Preparation of a Sensor Chip 3 According to a Comparative Example and Evaluation of Performance thereof Spin coating was conducted by the same method as in Example 1 except that, in the production of the polymer-A-coated chip in Example 1(3), the aluminum container was sealed and the substrate was rotated after the 3 second rest period. The solvent vapor pressure inside the aluminum container immediately before the start of rotation was 40% with respect to the saturation vapor pressure. Based on ellipsometric measurement, the average film thickness was found to be 20 nm and the variation coefficient of the film thickness (a percentage value of the standard deviation divided by the average value) was found to be 12%. Further, the operations (4) to (6) of Example 1 were carried out.

Comparative Example 4

Preparation of a Sensor Chip 4 According to a Comparative Example and Evaluation of Performance thereof Spin coating was conducted by the same method as in Example 2 except that, in the production of the polymer-A-coated chip in Example 2, the aluminum container was sealed and the substrate was rotated after the 3 second rest period. The solvent vapor pressure inside the aluminum container immediately before the start of rotation was 30% with respect to the saturation vapor pressure. Based on ellipsometric measurement, the average film thickness was found to be 20 nm and the variation coefficient of the film thickness (a percentage value of the standard deviation divided by the average value) was found to be 12%. Further, the operations (4) to (6) of Example 1 were carried out.

(7) Results

Table 1 shows the signal changes due to the mouse IgG binding depending on the position within the chips. CV indicates the variation coefficient (a percentage value of the standard deviation divided by the average value).

TABLE 1

| | Signal change (RU) | | | | | | | | |
|---|---|---|---|---|---|---|---|---|---|
| Lateral distance | 10 mm | 20 mm | 30 mm | 40 mm | 50 mm | 60 mm | 70 mm | Average value | CV (%) |
| Ex. 1 | 590 | 610 | 610 | 600 | 620 | 620 | 610 | 610 | 2 |
| Ex. 2 | 550 | 570 | 610 | 600 | 590 | 620 | 590 | 590 | 4 |
| Comp. Ex. 1 | 570 | 620 | 480 | 600 | 620 | 430 | 610 | 560 | 14 |
| Comp. Ex. 2 | 580 | 400 | 610 | 440 | 610 | 300 | 600 | 510 | 25 |
| Comp. Ex. 3 | 570 | 600 | 500 | 590 | 610 | 420 | 590 | 550 | 13 |
| Comp. Ex. 4 | 550 | 480 | 580 | 600 | 590 | 400 | 600 | 540 | 13 |

It can be seen from the results shown in Table 1 that the spin-coated chips according to the examples of the invention have smaller film thickness distributions of the Polymer A film in the chips, and that there are fewer variations in signal change depending on position.

EFFECT OF THE INVENTION

The method of the present invention enables formation of a thin film with a small film thickness distribution on a substrate. That is, the present invention provides a solid substrate for sensors having a film with a small film thickness distribution, and particularly, a solid substrate for sensors, the surface of which is coated with a thin polymer film. Using a solid substrate for sensors produced by the method of the present invention, it becomes possible to conduct measurement with suppressed deviation in sensor detection sensitivity.

The invention claimed is:

1. A method for producing a solid substrate for sensors that has a coating on the surface using spin coating, wherein a substrate to be coated is rotated in an atmosphere in which the vapor pressure of coating solvent is 50% to 100% with respect to the saturation vapor pressure so as to form a thin film of a coating solution on said substrate to be coated;
    wherein said substrate to be coated is set on an inner cup at a position such that the distribution of the centrifugal force on said substrate to be coated, which is produced by the rotation of an inner cup, is such that the maximum centrifugal force on said substrate is 100 times or less the minimum centrifugal force on said substrate, the coating solution is added dropwise onto the surface of said substrate to be coated, and then said substrate to be coated is rotated.

2. The method according to claim 1, wherein said substrate to be coated is introduced into a sealed container, and said substrate to be coated is rotated in an atmosphere in which the vapor pressure of coating solvent is 50% to 100% with respect to the saturation vapor pressure.

3. The method according to claim 2, wherein the volume of said sealed container into which said substrate to be coated is introduced is 3 to 1000 times the volume of the coating solution with which the surface of said substrate to be coated is coated.

4. The method according to claim 1, wherein the surface of said substrate to be coated is coated with the coating solution, said substrate to be coated is introduced into a container having a sealed structure, said substrate to be coated is kept in a substantially non-rotating state for 10 to 4000 seconds, and then said substrate to be coated is rotated so as to form a thin film on the substrate.

5. The method according to claim 1, wherein the maximum centrifugal force on said substrate is 10 times or less the minimum centrifugal force on said substrate.

* * * * *